United States Patent [19]

Zorgniotti et al.

[11] 4,253,464
[45] Mar. 3, 1981

[54] METHOD AND DEVICE FOR CONTRIBUTING TO THE OBVIATING OF MALE INFERTILITY

[75] Inventors: Adrian W. Zorgniotti, New York; Andrew I. Sealfon, Middletown, both of N.Y.

[73] Assignee: Repro Med Systems, Inc., Middletown, N.Y.

[21] Appl. No.: 78,147

[22] Filed: Sep. 24, 1979

[51] Int. Cl.³ .................................................. A61F 7/00
[52] U.S. Cl. ....................................... 128/400; 128/1 R
[58] Field of Search .................. 2/403; 128/1 R, 68.1, 128/79, 289, 294, 295, 296, 290, 291, 400, 401, 402, 403, 82.1, 362, DIG. 27, 399

[56] References Cited

U.S. PATENT DOCUMENTS

| 26,663 | 1/1860 | French | 128/403 |
|---|---|---|---|
| 734,213 | 7/1963 | Barnes | 128/402 |
| 2,864,369 | 12/1958 | Morrow | 128/295 |
| 3,075,517 | 1/1963 | Morehead | 128/400 |
| 3,079,765 | 3/1963 | Le Vantine | 128/402 |
| 3,940,943 | 3/1976 | Sikes et al. | 128/1 R |
| 3,998,210 | 12/1976 | Nosari | 128/771 |

FOREIGN PATENT DOCUMENTS

| 815732 | 6/1969 | Canada | 128/400 |
|---|---|---|---|
| 757338 | 9/1971 | France | 128/1 R |

OTHER PUBLICATIONS

"Sperm Don't Like it Hot", Joan Avehart-Treichel, Science News, May 11, 1974, vol. 105, pp. 309 and 310.
Textbook of Medical Physiology-A. C. Guyton, M.D., Make Fertility, W. B. Saunders Co., Philadelphia, Pa., 1971, pp. 948-949.

Primary Examiner—Robert W. Michell
Assistant Examiner—J. L. Kruter
Attorney, Agent, or Firm—Bauer & Amer

[57] ABSTRACT

Using latent heat of vaporization of a selected evaporative fluid, an abnormally elevated testicular temperature is effectively diminished so as to contribute to obviating male infertility due to poor semen quality. Moreover, the evaporative method employed, and the device using such method, are particularly appropriate in that the cooling effect is achieved over a prolonged period so as to facilitate achieving the desired medical result, whereas merely diminishing the testicular temperature for a short duration would not be medically effective.

4 Claims, 3 Drawing Figures

METHOD AND DEVICE FOR CONTRIBUTING TO THE OBVIATING OF MALE INFERTILITY

The present invention relates generally to product and method improvements for a recommended treatment for male infertility due to poor semen quality, and more particularly to an effective lower torso garment, and operational mode in a cooling component thereof, for effectively producing an intrascrotal temperature reduction, of as much as 3 degrees centigrade, in the testis.

Infertile marriages due to poor semen quality are known to be attributable to an abnormally elevated testicular temperature. As an alternative to a surgical cure, i.e. a varicocelectomy, it is desirable to achieve a temperature reduction of 1 to 3 degrees centigrade, and thus enable the semen to be produced in an optimum temperature range of 31 to 33 degrees centigrade in such infertile males. However, presently known therapeutic wraps or devices for chilling body areas, as exemplified by the wrap of U.S. Pat. No. 4,092,982, are not effective. Not only are such prior art body-chilling devices too cumbersome and uncomfortable for the localized use herein required, but their chilling effect is not compatible with being applied over prolonged periods of treatment, which typically might be as much as 16 hours per day for six to twenty weeks of treatment. The above referred to patented wrap, for example, uses a refrigerant gel which would be too inconvenient to replenish, as well as being otherwise inappropriate, if adopted for the specific end use as above noted.

Broadly, it is an object of the present invention to provide a device, effective both in its product and method aspects, for producing a desired intrascrotal temperature reduction overcoming the foregoing and other noted shortcomings of the prior art. Specifically, it is an object to effectively withdraw heat, over a selected prolonged duration, so as to effectuate a correspondingly selected intrascrotal temperature reduction, using a lower torso garment or appliance that offers nominal discomfort or interference with normal activity.

Demonstrating method aspects of the present invention is a method that contributes to minimizing male infertility due to abnormally elevated testicular temperature including the supporting on a lower torso garment of an absorbent member presenting a cooling surface in position adjacent to and in surrounding relation about the periphery of the testis. Additionally supported on the lower torso garment is a source of evaporative fluid, either water, ethyl alcohol, or a mixture thereof. The within method contemplates continuously flowing from said evaporative fluid source to said absorbent member through a capillary means, of an appropriate selected size to provide at least 7 grams per hour flow, of the evaporative fluid so as to achieve the evaporative release thereof from the cooling surface. As a result, calories in an amount corresponding to the latent heat of vaporization of the evaporative fluid, are removed from the testis, and this in practice has been found to effectively diminish the otherwise abnormally elevated intrascrotal temperature so as to obviate poor semen quality as a cause of male infertility.

The above brief description, as well as further objects, features and advantages of the present invention, will be more fully appreciated by reference to the following detailed description of a presently preferred, but nonetheless illustrative embodiment demonstrating both the method and device aspects in accordance with the present invention, when taken in conjunction with the accompanying drawings, wherein.

As understood, male infertility may be due to an abnormally elevated intrascrotal temperature which, in turn, has an adverse effect on the quality of semen in terms of reproduction, i.e. those qualities of the semen such as sperm count, motility and a high percentage of morphologically normal spermatoza. That is, with an elevation of as little as 1 to 3 degrees centigrade from an acceptable intrascrotal temperature range of between 31 to 33 degrees centigrade, male patients often seek treatment for infertile marriage attributable to semen quality. This treatment is very often achieved surgically, by a so-called varicocelectomy, which attempts to neutralize the retrograde blood flow via the testicular vein that otherwise would raise the testicular temperature to the extend of the interference the causes with counter-current heat exchange flow with the testicular artery. In many patients, however, the surgical procedure is not palpable, for one reason or another, or does not produce the desired result.

As an alternative to a surgical procedure for patients seeking treatment for infertile marriage the present invention comtemplates a method and device for effectively achieving the desired 1 to 3 degree centigrade diminishment of an abnormally elevated testicular temperature. Moreover, while it is known within the field of therapeutic wrap devices, as exemplified by that of prior U.S. Pat. No. 4,092,982, that such wraps are useful for heat removal from body areas in which there may have occurred a rupture or laceration, etc., and rely for this purpose on the use of a refrigerant gel or similar body-chilling medium, the referred to prior art technology is not adaptable for use in achieving temperature diminishment of the testis. Underlying the present invention is the recognition that an acceptable method of heat removal from this body area can be effectively achieved using an evaporative fluid having an appropriate latent heat of vaporization to effectuate the 1 to 3 degree centigrade temperature diminishment. Further, and most important, also underlying the method aspects of the within invention is the recognition that heat removal using an evaporative fluid is particularly advantageous for the intended end use because heat removal by same is achieved over a desirable prolonged period of time, since this merely requires providing an appropriate volume of the evaporative fluid to achieve this objective. Thus, the within inventive method can effectively serve as an acceptable treatment for the medical problem that is involved. Stated another way, the semen is produced over a period of time during which it is required that the intrascrotal temperature be in the proper range as noted, and thus a cooling method which merely lowered the testicular temperature for only a short time duration would not achieve any significant medical result.

Figure 1:
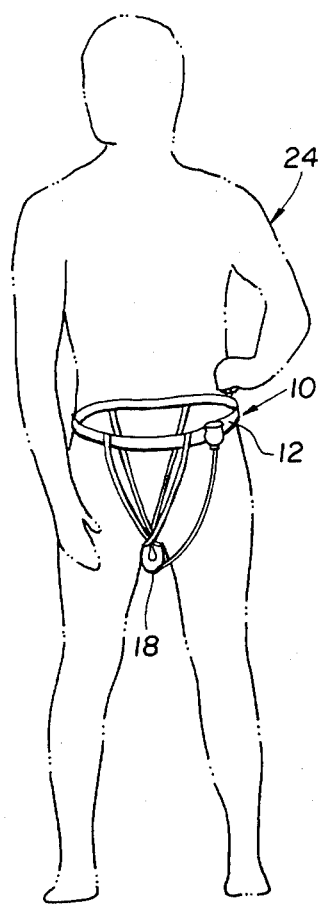
FIG. 1 is a perspective view illustrating the contemplated manner in which the inventive device hereof is intended to be used.
Figure 2:
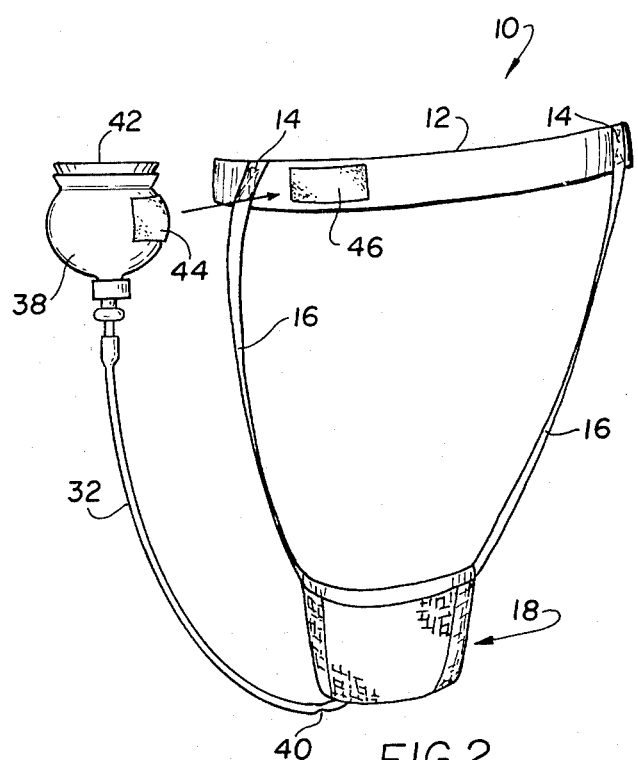
FIG. 2 is a side elevational view on an enlarged scale, illustrating structural details of the device.
Figure 3:
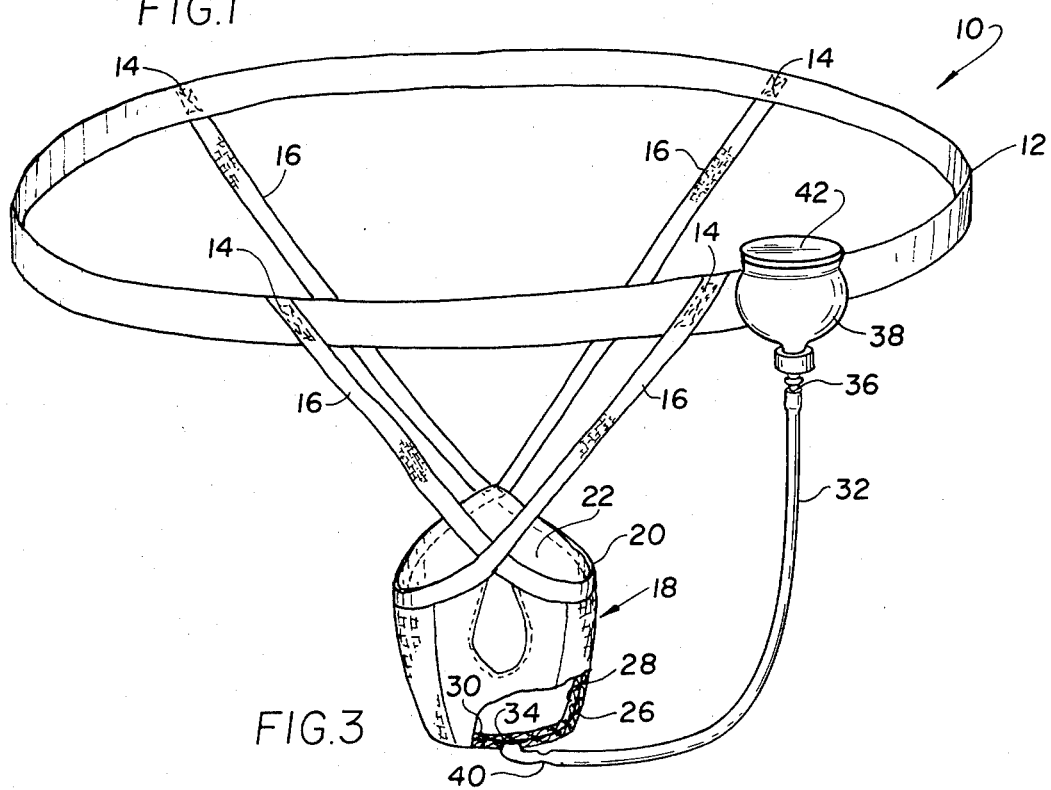
FIG. 3 is a perspective view of the device illustrating still further structural details, portions thereof being broken away and in section to illustrate structural details of the pouch component of the device.

Reference is now made to FIGS. 1–3 of an embodiment demonstrating both product and method aspects of the invention. As to product aspects, however, it is to be understood that while the components and their function are essential to the invention, that these components can take different and other forms. The form of the illustrated components was selected for description of the invention since they were used in field testing and in obtaining clinical data.

More particularly, and as illustrated in the drawings, the inventive device, generally designated 10, is intended in use to be worn about the lower torso and, to this end, includes a waist-encircling band 12. Attached, as at locations 14, to the waistband 12 so as to suspend in depending relation therefrom are supporting straps 16. A pouch 18, the specific construction of which will be subsequently described, is supported from the closed end of the straps 16, said closed ends being more particularly designated 20 and serving, as is perhaps most clearly illustrated in FIG. 3, as the upper edges bounding the opening into a compartment 22 of the pouch 18.

As may be readily appreciated from FIG. 1, in conjunction with FIGS. 2 and 3, the lower torso garment or appliance 10 is worn so that the pouch 18 occupies a position in surrounding relation to the testis (not designated) of the male patient 24.

As is perhaps best illustrated in the cross-section of FIG. 3, a preferred construction for the pouch 18 consists of a knitted fabric serving as the outer cover 26 and an inner liner 28 of an absorbent cotton or similar material, wherein the liner 28 presents a surface 30 that is adjacent to and in facing relation to the patient's testis. In the manner as will now be described, surface 30 supplies the necesary cooling effect which results in the diminishment in practice of between 1 to 3 degrees centigrade in the intrascrotal or testicular temperature, such that the semen of the patient 24 is produced in a desired temperature environment of between 31 to 33 degrees centigrade.

To embody cooling surface 30 with the capability of achieving temperature diminishment as just noted, there is connected in cooperating relationship therewith a capillary tube 32 appropriately connected, as at 34, to the absorbent body or liner 28 and, at its other end, as at 36, to a glass or plastic fluid container 38. A metering orifice, in the preferred form of a crimp 40 in the tube 32, restricts flow to a rate that is related to the absorbency of the cotton body 28 and the evaporative release from the surface 30 of the fluid that is stored in the container 38 and allowed to flow through the capillary tube 32.

Clinical testing of the device 10 indicates that when using water as the evaporative fluid in the container 38, that when the temperature-humidity index was below 70 there was achieved a flow rate of at least 7 grams per hour through the tube 32, and that this flow rate produced the desired result. More particularly, the latent heat of vaporization of water is 540 calories per gram and at the flow rate of at least 7 grams per hour there resulted a cooling effect of approximately 3800 calories per hour which effectively diminished the abnormally elevated testicular temperature of the patient 24 to within an acceptable temperature range so as to contribute to obviating male infertility due to poor semen quality.

Said clinical testing also indicated that when the temperature-humidity index was significantly in excess of 70, that heat removal was not only required of the abnormally elevated testicular temperature, but also that the temperature increase has to be offset that is occasioned when humidity increases and the rate of evaporization of any fluid correspondingly decreases. In these circumstances the evaporative fluid selected was ethyl alcohol, either mixed with water or used pure. Since ethyl alcohol evaporates at the lower latent heat value of 204 calories per hour, more of this fluid is required to achieve the same cooling effect achieved with water. Using the same diameter size tube 32 with its metering orifice or crimp 40, it was found that the same favorable results of diminishing the intrascrotal temperature at least 1 to 3 degrees centigrade was readily achieved. From this it was surmised that the flow rate of the ethyl alcohol was one-and-a-half times the 7 grams per hour of the water, undoubtedly due to the difference in density and surface tension of this fluid as compared with water, and that this increased flow rate more than made up for the approximately 50% less effective cooling effect of this fluid as compared with water. In summary, the within system relying on flow by capillary action through the tube 32, i.e. flow in response to evaporation at the cooling surface 30 insofar as said flow is replenishment thereof, is effective to produce at least a flow of 7 grams per hour of the evaporative fluid, and that such flow rate is in turn effective to provide the temperature diminishment that is required to produce the desired medical effect.

As is best shown in FIG. 2, completing the construction of a preferred embodiment for the lower torso garment or device 10 is a closure 42 that is force-fit in the opening of the container 38, and interconnecting patches of "velcro" for supporting container 38 on the waistband 12, one patch 44 being adhesively secured to the container 38 and the other patch 46 being appropriately attached to the waistband 12.

From the foregoing description it should be readily appreciated that device 10, considered from its product aspects, offers minimal discomfort and inconvenience to the patient 24. Further, considered from its method aspects, the operational mode of device 10 is one which effectively supplies a cooling effect to the human testis over a prolonged period of time and thus during the production by the patient 24 of semen and, to this end, is therefore effective in providing the necessary temperature environment which contributes to obviating infertility as might otherwise be due to poor semen quality.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. A method contributing to minimizing male infertility due to abnormally elevated testicular temperature comprising the steps of supporting on a lower torso garment an absorbent member presenting a cooling surface in position adjacent to and in surrounding relation about the periphery of the testis, additionally supporting on said lower torso garment a source of evaporative fluid, and continuously flowing from said evaporative fluid source to said absorbent member through a capillary means selected to provide at least seven grams per hour of said evaporative fluid for evaporative release from said cooling surface, whereby the calories in an amount corresponding to the latent heat of vaporization of said evaporative fluid are removed from the testis to diminish said otherwise abnormal elevated temperature thereof.

2. The method of treating male infertility as defined in claim 1 wherein the preferred evaporative fluid is water when the ambient temperature and humidity index is below 70.

3. The method of treating male infertility as defined in claim 1 wherein the preferred evaporative fluid is ethyl alcohol when the ambient temperature and humidity index is to a significant extend above 70.

4. A lower torso garment for use in treating male infertility due to abnormally elevated testicular temperature comprising a waist-encircling band, a pouch supported in depending relation from said band so as to assume a surrounding position about the wearer's testis, a fluid-absorbing body disposed in said pouch having a cooling surface in facing relation to said testis, a container for a volume of selected evaporative fluid supported on said band, and a selected size capillary tube connected to flow at least seven grams per hour of said evaporative fluid for evaporative release at said cooling surface, whereby said garment produces a desired localized cooling effect during wearing service.

* * * * *